US011813029B2

(12) United States Patent
Robinson

(10) Patent No.: US 11,813,029 B2
(45) Date of Patent: *Nov. 14, 2023

(54) SYSTEM FOR CUTTING ELEMENT POSITION INDICATION

(71) Applicant: INTUITIVE SURGICAL OPERATIONS, INC., Sunnyvale, CA (US)

(72) Inventor: David W. Robinson, Los Altos, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 274 days.

This patent is subject to a terminal disclaimer.

(21) Appl. No.: 17/110,246

(22) Filed: Dec. 2, 2020

(65) Prior Publication Data

US 2021/0077202 A1    Mar. 18, 2021

Related U.S. Application Data

(63) Continuation of application No. 16/253,612, filed on Jan. 22, 2019, now Pat. No. 10,881,469, which is a
(Continued)

(51) Int. Cl.
*A61B 34/20* (2016.01)
*A61B 34/30* (2016.01)
(Continued)

(52) U.S. Cl.
CPC .............. *A61B 34/20* (2016.02); *A61B 18/14* (2013.01); *A61B 18/1445* (2013.01);
(Continued)

(58) Field of Classification Search
CPC ... A61B 17/072; A61B 18/14; A61B 18/1445; A61B 18/1482; A61B 34/20;
(Continued)

(56) References Cited

U.S. PATENT DOCUMENTS

| 5,599,350 A | 2/1997 | Schulze et al. |
| 5,950,629 A | 9/1999 | Taylor et al. |

(Continued)

FOREIGN PATENT DOCUMENTS

| CN | 101068500 A | 11/2007 |
| EP | 0776739 A2 | 6/1997 |

(Continued)

OTHER PUBLICATIONS

Extended European Search Report for Application No. EP21200303.2, dated Jan. 11, 2022, 10 pages.

(Continued)

*Primary Examiner* — Jocelin C Tanner
(74) *Attorney, Agent, or Firm* — Artegis Law Group, LLP

(57) ABSTRACT

Systems and methods for cutting element indication include an end effector having a jaw for clamping a material and a cutting element within the end effector and a processor. The cutting element is moveable relative to the end effector. The cutting element is driven by a drive element and a mechanism coupling the drive element to the cutting element. The processor is configured to determine a position of the cutting element relative to the end effector via a displacement of the drive element and a displacement of the mechanism and display, on a user interface, an indicator of the position of the cutting element relative to the end effector.

20 Claims, 13 Drawing Sheets

Related U.S. Application Data continuation of application No. 13/350,522, filed on Jan. 13, 2012, now Pat. No. 10,194,992.

(60) Provisional application No. 61/443,115, filed on Feb. 15, 2011.

(51) Int. Cl.
  *A61B 18/14* (2006.01)
  *A61B 17/00* (2006.01)
  *A61B 17/072* (2006.01)
  *A61B 90/98* (2016.01)
  *A61B 90/00* (2016.01)

(52) U.S. Cl.
  CPC .............. *A61B 34/30* (2016.02); *A61B 90/98* (2016.02); *A61B 2017/00022* (2013.01); *A61B 2017/00398* (2013.01); *A61B 2017/07285* (2013.01); *A61B 2018/1455* (2013.01); *A61B 2034/2051* (2016.02); *A61B 2034/2059* (2016.02); *A61B 2090/0803* (2016.02)

(58) Field of Classification Search
  CPC .................. A61B 34/30; A61B 90/37; A61B 2017/00022; A61B 2017/00119; A61B 2017/00398; A61B 2017/07285; A61B 2018/00607; A61B 2018/1455; A61B 2034/2051; A61B 2034/2059; A61B 2090/0803
  See application file for complete search history.

(56) References Cited

U.S. PATENT DOCUMENTS

| | | | |
|---|---|---|---|
| 6,468,265 | B1 | 10/2002 | Evans et al. |
| 7,155,315 | B2 | 12/2006 | Niemeyer et al. |
| 9,526,587 | B2 | 12/2016 | Zhao et al. |
| 9,718,190 | B2 | 8/2017 | Larkin et al. |
| 9,867,669 | B2 | 1/2018 | Zhao et al. |
| 10,194,992 | B2 * | 2/2019 | Robinson ............... A61B 34/20 |
| 10,881,469 | B2 * | 1/2021 | Robinson ............... A61B 34/20 |
| 2002/0165444 | A1 | 11/2002 | Whitman |
| 2003/0105478 | A1 * | 6/2003 | Whitman ............ A61B 17/068 |
| | | | 606/167 |
| 2003/0163040 | A1 | 8/2003 | Gildenberg et al. |
| 2006/0184011 | A1 | 8/2006 | MacAulay et al. |
| 2006/0258938 | A1 | 11/2006 | Hoffman et al. |
| 2006/0258955 | A1 | 11/2006 | Hoffman et al. |
| 2007/0175949 | A1 | 8/2007 | Shelton, IV et al. |
| 2007/0225550 | A1 | 9/2007 | Gattani et al. |
| 2007/0255106 | A1 | 11/2007 | Kawanishi |
| 2008/0029576 | A1 | 2/2008 | Shelton et al. |
| 2008/0104855 | A1 | 5/2008 | Kim et al. |
| 2008/0296346 | A1 | 12/2008 | Shelton, IV et al. |
| 2009/0076534 | A1 * | 3/2009 | Shelton, IV ..... A61B 17/07207 |
| | | | 713/193 |
| 2009/0192523 | A1 | 7/2009 | Larkin et al. |
| 2009/0289096 | A1 | 11/2009 | Shelton, IV et al. |
| 2009/0326531 | A1 * | 12/2009 | Geiselhart ............ A61B 17/295 |
| | | | 606/170 |
| 2010/0198220 | A1 | 8/2010 | Boudreaux et al. |
| 2010/0228250 | A1 | 9/2010 | Brogna |
| 2010/0256635 | A1 | 10/2010 | McKenna et al. |
| 2011/0155781 | A1 | 6/2011 | Swensgard et al. |
| 2012/0022529 | A1 | 1/2012 | Shelton, IV et al. |
| 2012/0143182 | A1 * | 6/2012 | Ullrich ............... A61B 18/1445 |
| | | | 606/49 |
| 2012/0191091 | A1 | 7/2012 | Allen |
| 2019/0151029 | A1 | 5/2019 | Robinson |

FOREIGN PATENT DOCUMENTS

| | | |
|---|---|---|
| JP | 2005518854 A | 6/2005 |
| JP | 2008036426 A | 2/2008 |
| JP | 2009533175 A | 9/2009 |
| WO | WO-2006058302 A1 | 6/2006 |
| WO | WO-2008002830 A2 | 1/2008 |
| WO | WO-2009143092 A1 | 11/2009 |
| WO | WO-2010110560 A2 | 9/2010 |
| WO | WO-2010151438 A1 | 12/2010 |

OTHER PUBLICATIONS

Extended European Search Report for Application No. EP17189474. 4, dated Dec. 11, 2017, 9 pages (ISRG03020D1/EP).
International Search Report and Written Opinion for PCT/US2012/021336, dated Mar. 30, 2012, 15 pages.
Office Action dated Apr. 21, 2015 for Chinese Application No. 2012808768 filed Jan. 13, 2012, 17 pages (ISRG03020/CN).
Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

* cited by examiner

SYSTEM FOR CUTTING ELEMENT POSITION INDICATION

CROSS-REFERENCES TO RELATED APPLICATIONS

The present application is continuation of U.S. patent application Ser. No. 16/253,612, filed Jan. 22, 2019 and entitled "System for Moveable Element Position Indication," which is continuation of U.S. patent application Ser. No. 13/350,522, filed Jan. 13, 2012 and entitled "Indicator for Knife Location in a Stapling or Vessel Sealing Instrument," which claims the benefit of U.S. Provisional Patent Application No. 61/443,115, filed Feb. 15, 2011 and entitled "Indicator for Knife Location in a Stapling or Vessel Sealing Instrument," each of which is incorporated herein by reference.

This application is related to the following applications: U.S. application Ser. No. 12/705,418, entitled "Cut and Seal Instrument", filed on Feb. 12, 2010; U.S. application Ser. No. 12/415,332, filed on Mar. 31, 2009; and U.S. application Ser. No. 11/478,531, filed on Jun. 29, 2006, each of which is hereby incorporated by reference.

BACKGROUND OF THE INVENTION

Minimally invasive surgeries performed by robotic surgical systems are known and commonly used in clinical procedures where it is advantageous for a human not to perform surgery directly. One example of such a system is the minimally invasive robotic surgery system described in commonly owned U.S. Pat. No. 7,155,315, entitled "Camera Referenced Control in a Minimally Invasive Surgical Apparatus."

A common form of minimally invasive surgery is endoscopy. Endoscopic surgical instruments in minimally invasive medical techniques generally include an endoscope for viewing the surgical field, and working tools defining end effectors. Typical surgical end effectors include clamps, graspers, scissors, tissue cutters, staplers, or needle holders, as examples. The working tools are similar to those used in conventional (open) surgery, except that the end effector of each tool is supported on the end of, for example, an approximately 12-inch-long extension tube. To manipulate end effectors, a human operator, typically a surgeon, manipulates or otherwise commands a master manipulator. Commands from the master manipulator are translated as appropriate, and sent to a slave manipulator. The slave manipulator then manipulates the end effectors according to the user's commands. As the surgeon is somewhat removed from the movement of the end effector, the surgeon generally relies on feedback mechanisms, such as an endoscopic imaging, to determine the locations of the surgical tools within a patient's body. In general, in telesurgical systems, the surgeon is provided an "internal user interface." This internal user interface includes a display that can be seen by the surgeon during the procedure.

Among the procedures performed in minimally invasive surgeries is the resection of tissue, which may include clamping, sealing and cutting of a body tissue. In a tissue sealing and cutting procedure, the end effector has mechanisms for sealing the tissue (e.g. RF energy, sutures, staples, etc.) and a cutting member (e.g. tissue cutter, blade, ablative energy). Typically, a sealing and cutting procedure involves the steps of clamping a tissue, sealing the clamped tissue on either side of a cutting line, then cutting the clamped tissue along the cutting line. If for any reason, the cutting process should stall or fail, this may present a hazard since the cutting member may remain in an exposed position. Removal of the end effector with the cutting member in this position may result in inadvertent cutting of other tissues proximal of the device or may present a hazard to the surgeon or other surgical staff once the tool is removed. Since cutting failure is a low occurrence event, and the surgeon's view of the cutting element may be obscured by the end effector, a surgeon may not maintain an accurate mental model of how the cutting element is positioned and moved, and may be unaware of the hazard presented by an exposed cutting element.

It would be desirable for systems and methods which provide indications and images that allow a physician to visualize and, more importantly, to habitualize themselves with the position and location of the tissue cutter during a procedure. Such methods would enable physicians to develop a intuitive "sense" for the how the tissue cutter operates so as to facilitate cutting and prevent potential tissue damage.

BRIEF SUMMARY OF THE INVENTION

Improved systems and methods for indicating a position of a tool of an end effector are provided. The claimed methods and systems relate to displaying an image of a motor-driven tool clamping a material on a user interface, the tool having a first and second jaw for clamping the material and a cutting element (e.g. a knife or blade) for cutting the material, and superimposing on the user interface display a visual indicator of a position of the cutting element. The cutting element (e.g. blade, knife) comprises various positions, wherein a position represents a position and/or an orientation of the cutting element. In many embodiments, the tool comprises an end effector having a first and second jaw and a knife disposed within the end effector such that the knife moves along a longitudinal axis of the jaws from a pre-cut position to a cut-complete position, thereby cutting the tissue clamped between the jaws. The knife positions may include any or all of: a pre-cut position, a cut-complete position, a cut-incomplete position, and a exposed position. The described methods allow a user to visualize or sense the location and/or orientation of the knife of the end effector, even when the knife may not be visible due to interference from the material or the jaws of the end effector, which is particularly useful in a minimally invasive robotic surgical procedure. The methods and systems are advantageous as they allow surgeons to become habitualized with the movement of the knife during cutting, thereby improving the surgeon's intuitive sense of the procedure. This is particularly useful on the rare occasion when the movement of the knife should stall leaving the knife in an "exposed" or "cut-incomplete" position, which may potentially cause inadvertent tissue damage if the surgeon is unaware of the hazard. While the various embodiments disclosed herein are primarily described with regard to surgical applications, these surgical applications are merely example applications, and the disclosed end effectors, tools, and methods can be used in other suitable applications, both inside and outside a human body, as well as in non-surgical applications.

In a preferred embodiment, an indication of knife position is superimposed on the display during and/or after a cutting procedure, and more preferably at all times during the procedure. The indication may comprise any visual indicator sufficient to communicate the position of the knife to a user. The knife position may further include the location of the knife on the end effector and/or an orientation of the knife. Ideally, the indicator of knife position includes a synthetic representation of the knife superimposed on the image of the end effector at a location corresponding to the actual knife location and orientation on the end effector.

In an embodiment, the method includes tracking a moveable element in an environment, wherein at least a portion of the element is hidden from view in an image of the environment displayed on a user interface during a procedure and displaying on the user interface an indicator of a position of the element. The portion of the element hidden from view may be visible at other times during the procedure. Additionally, the portion of the element which is hidden from view may change during the procedure, such as when the element is moved through the environment or when tissue or other tool components visible in the environment move relative to the element. Tracking the element may include determining a location or an orientation of the element, often determined relative to a tool moveably coupled to the element. In many embodiments, the element comprises a cutting blade for cutting a body tissue of a patient coupled to the tool which is inserted into a body cavity of a patient, such as in a minimally invasive surgical procedure. Tracking the element may include tracking a mechanism moving the element or processing images of positional markers disposed on the element. The indicator of the position of the element may be displayed on the user interface so as to habitualize a user to the position as the element moves between a plurality of positions. In some embodiments, the indicator of position may provide an alternate indication in response to a trigger condition, such as an indication that the element has stopped when the element unexpectedly stops between a first and second position. Displaying the indicator on the user interface may include displaying a representation of the element on the display, such as a synthetic representation of the element on a video image of the environment and/or the tool. Preferably, the indicator of position is dynamic such that the indicator conveys the motion of the element allowing the user to see and become accustomed to the movement of the element during a procedure.

In many embodiments, the methods and systems include clamping the tissue between a first and second jaw of the tool, and energizing a motor of the tool in response to a user command to clamp the tissue, the motor being operatively coupled to the knife so as to move the knife relative to the jaws between a pre-cut knife position and a cut-complete knife position, thereby cutting the tissue. Since the knife is typically disposed at least partially between the jaws, the jaws of the tool may inhibit viewing of the moving knife in an image of the tool during the procedure. Typically, the clamping and cutting occur in response to a user command to cut or clamp, however, cutting may also occur automatically after successful clamping. Typically, the tissue is clamped, then sealed on either side of a cutting line before cutting the tissue along the cutting line.

In an embodiment, the methods and system may include superimposing a warning indication of a knife position on the user interface during and/or after the cutting procedure, such as when the movement of the knife stalls leaving the knife exposed. The warning may be a separate indication from the above described indication of knife position so as to notify a user of a hazardous condition that may be caused by a stall or failure in cutting. For example, the display may include a warning light that lights when the knife is stalled or exposed in response to the knife stalling during the cutting procedure.

In an embodiment, the system includes a moveable element, a user interface display and a processor coupling the element to the user interface display so that the processor can output a visual indicator of a position of the element on the display. In many embodiments, the system further includes a tool moveably coupled to the element and an image capturing device, such as a video camera. The processor and/or the image capture device may be used to measure the location or orientation of the element relative to the tool or vice versa. The element is often moveable between a plurality of positions on the tool, preferably a first and second position. In many embodiments, the system processes positional information obtained by the processor (e.g. images from an image capture device) to determine the relative positions of the element and tool. The processor may be coupled to a mechanism effecting movement of the element so that the position of the element or the tool can be determined by the processor from a displacement of the mechanism.

In many embodiments, the tool includes an end effector having jaws for clamping a material and a cutting element (e.g. a knife or blade) for cutting the clamped material. Typically, the tool is a surgical tool having jaws for clamping tissue and a knife for cutting the clamped tissue. The knife is configured to move between the jaws from a pre-cut position to a cut-complete position, thereby cutting tissue clamped between the jaws. In the pre-cut and cut-complete position, a cutting edge of the knife is disposed safely in the end effector so as to protect adjacent tissue. The knife may include additional knife positions between the pre-cut and cut-complete position, including but not limited to a "knife-exposed" position and a "cut-incomplete" position. A knife position may further include the position and/or orientation of the knife relative to the end effector.

In many embodiments, the user interface display is coupled with the processor and image capture device so as to display an image of the end effector of the tool and an indication of knife position. If for any reason the tool is not visible, the user will be able to view an indicator of location and representation of the knife superimposed on an image of the tool. In a preferred embodiment, the indicator of knife position includes a synthetic representation of the knife superimposed on an image, actual or synthetic, of the end effector. The display may also indicate a warning separate from the indicator of knife position that the knife has stalled and presents a hazard, such as a stalled configuration or an exposed cutting edge of the knife.

For a fuller understanding of the nature and advantages of the present invention, reference should be made to the ensuing detailed description and accompanying drawings. Other aspects, objects and advantages of the invention will be apparent from the drawings and detailed description that follows.

DETAILED DESCRIPTION OF THE INVENTION

In the following description, various embodiments of the present invention will be described. For purposes of explanation, specific configurations and details are set forth in order to provide a more thorough understanding of the embodiments. However, it will also be apparent to one skilled in the art that the present invention may be practiced without the specific details. Furthermore, well-known features may be omitted or simplified in order not to obscure the embodiment being described.

Improved systems and methods for indicating a location and/or an orientation of a cutting element on a tool during a cutting procedure are provided. The claimed methods and systems may be used in conjunction with other methods of tracking so as to allow a user to perceive a position or orientation of the cutting element relative to the tool. These methods and systems are usefully in robotic systems where a user may not be able to see the cutting element during cutting, which is particularly useful in minimally invasive surgical procedures using a motor-driven end effector. These methods are advantageous as they allow a surgeon, removed from the end effector, to develop a sense of how the cutting member moves in relation to the tool during the procedure. By creating a sensory indication of a position of the cutting member relative to the tool, the methods allow a surgeon to become accustomed to the location of the cutting member on the tool, such that, should the cutting procedure fail, the surgeon would be aware of a potential hazard presented by the cutting member and can take appropriate action to avoid the hazard. While the various embodiments disclosed herein are primarily described with regard to surgical applications, these surgical applications are merely example applications, and the disclosed end effectors, tools, and methods can be used in other suitable applications, both inside and outside a human body, as well as in non-surgical applications.

Figure 1:
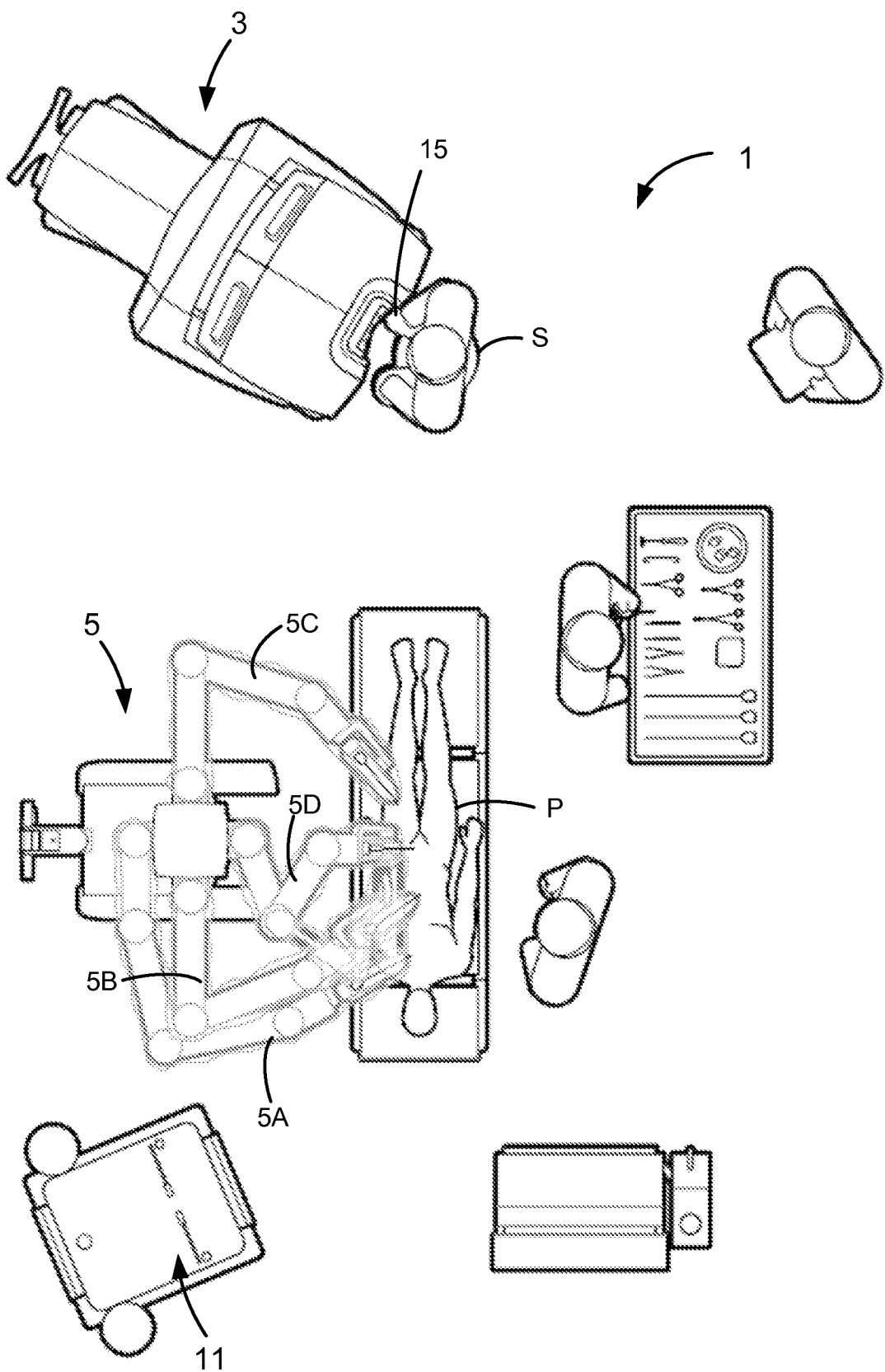
FIG. 1 shows a top view of an operating room which includes a minimally invasive telesurgical system in accordance with many embodiments.

Referring now to the drawings, in which like reference numerals represent like parts throughout several views, FIG. 1 shows a minimally invasive telesurgical system 1 having an operator station or surgeon console 3 in accordance with many embodiments. The surgeon console 3 includes a display 15 where an image of a surgical site is displayed to a surgeon S. As is known, a support (not shown) is provided on which the surgeon S can rest his or her forearms while gripping two master controls, one in each hand. Although more controls may be provided if more end effectors are available, typically a surgeon manipulates only two controls at a time; if multiple end effectors are used, the surgeon releases one end effector with a master control and grasps another with same master control. When using surgeon console 3, the surgeon S typically sits in a chair in front of the surgeon console, positions his or her eyes in front of the display 5, and grips the master controls, one in each hand, while resting his or her forearms on the support.

Figure 2:
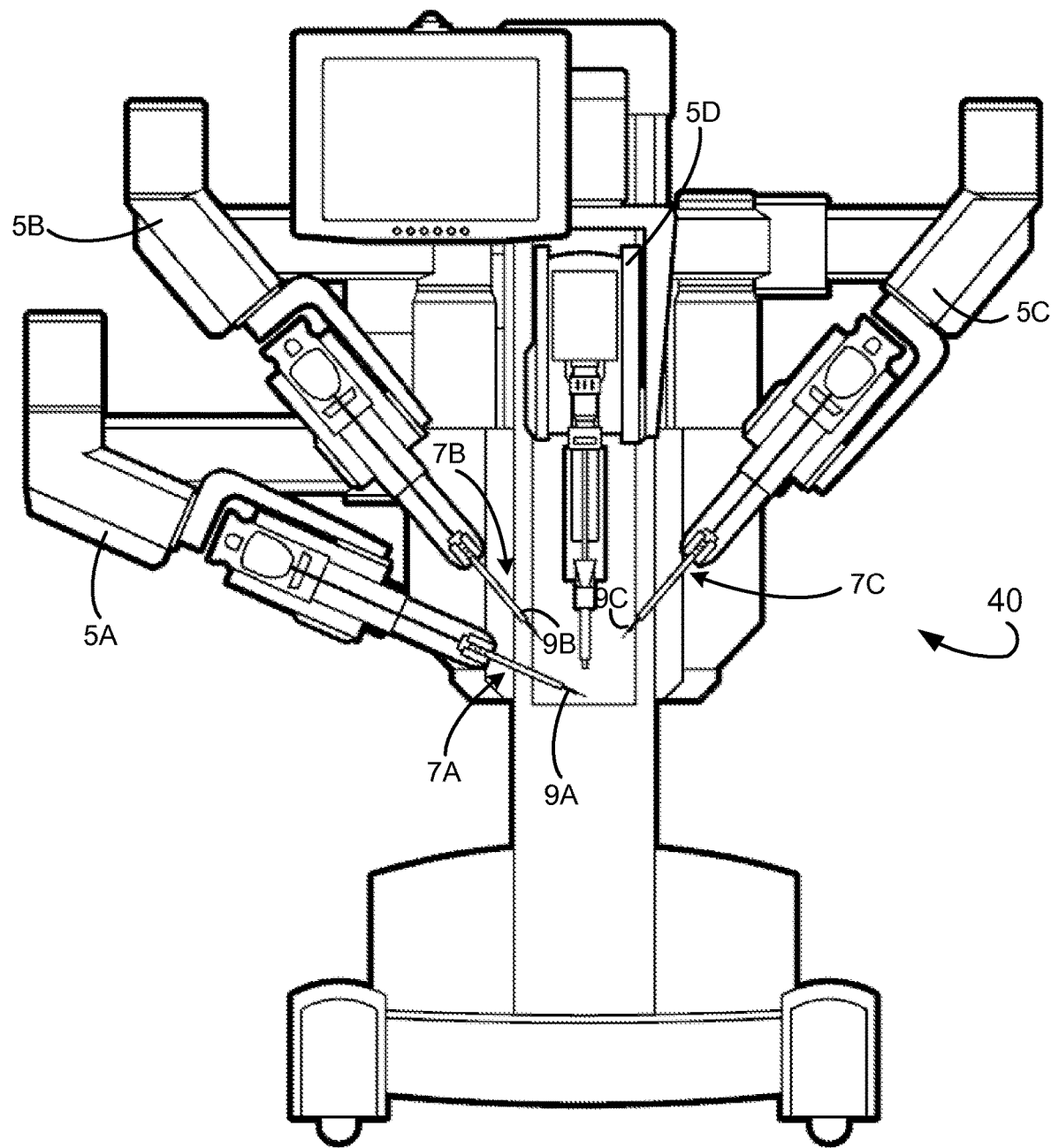
FIG. 2 is a front view of a patient cart for the minimally invasive telesurgical system of FIG. 1.

A patient side cart 5 of the telesurgical system 1 is positioned adjacent to a patient P. In use, the patient side cart 5 is positioned close to the patient P requiring surgery. The patient side cart 5 typically is stationary during a surgical procedure and includes robotic assemblies 5A, 5B, 5C, and 5D. The surgeon console 3 is typically positioned remote from the patient side cart 5 and may be separated from the patient side cart by a great distance, even miles away, but will typically be used within the same operating room as the patient cart. Each of the robotic arm assemblies 5A, 5B, and 5C includes a surgical instrument or tool 7A, 7B, and 7C, respectively. Assembly 5D may include an endoscope for imaging the tool on the display during the procedure. The tools 7A, 7B, and 7C of the robotic arm assemblies 5A, 5B, and 5C include end effectors 9A, 9B, and 9C, respectively. Movement of the end effectors 9A, 9B, and 9C relative to the ends of the shafts of the tools 7A, 7B, and 7C is also controlled by the master controls of the surgeon console 3. Any of tools 7A, 7B, and 7C may include a tissue cutting and sealing instrument. Such an instrument may comprise an end effector having jaws for clamping a tissue, a member for sealing the tissue (e.g., a stapling or RF mechanism), and a member for cutting the tissue after sealing (e.g., a movable blade, a knife, or any tissue cutting mechanism), an example of which is illustrated in FIGS. 4-7. FIG. 2 shows a front view of patient cart and the associated robotic arm assemblies.

The telesurgical system 1 includes a vision cart 11. In an embodiment, the vision cart 11 includes most of the computer equipment or other controls for operating the telesurgical system 1. As an example, signals sent by the master controllers of the surgeon console 30 may be sent to the vision cart 11, which in turn may interpret the signals and generate commands for the end effectors 9A, 9B, 9C and/or robotic arm assemblies 5A, 5B, 5C. In addition, video sent from an the image capturing device 5D, such as an endoscope, to the display 15 may be processed by, or simply transferred by, the vision cart 11.

Figure 3:
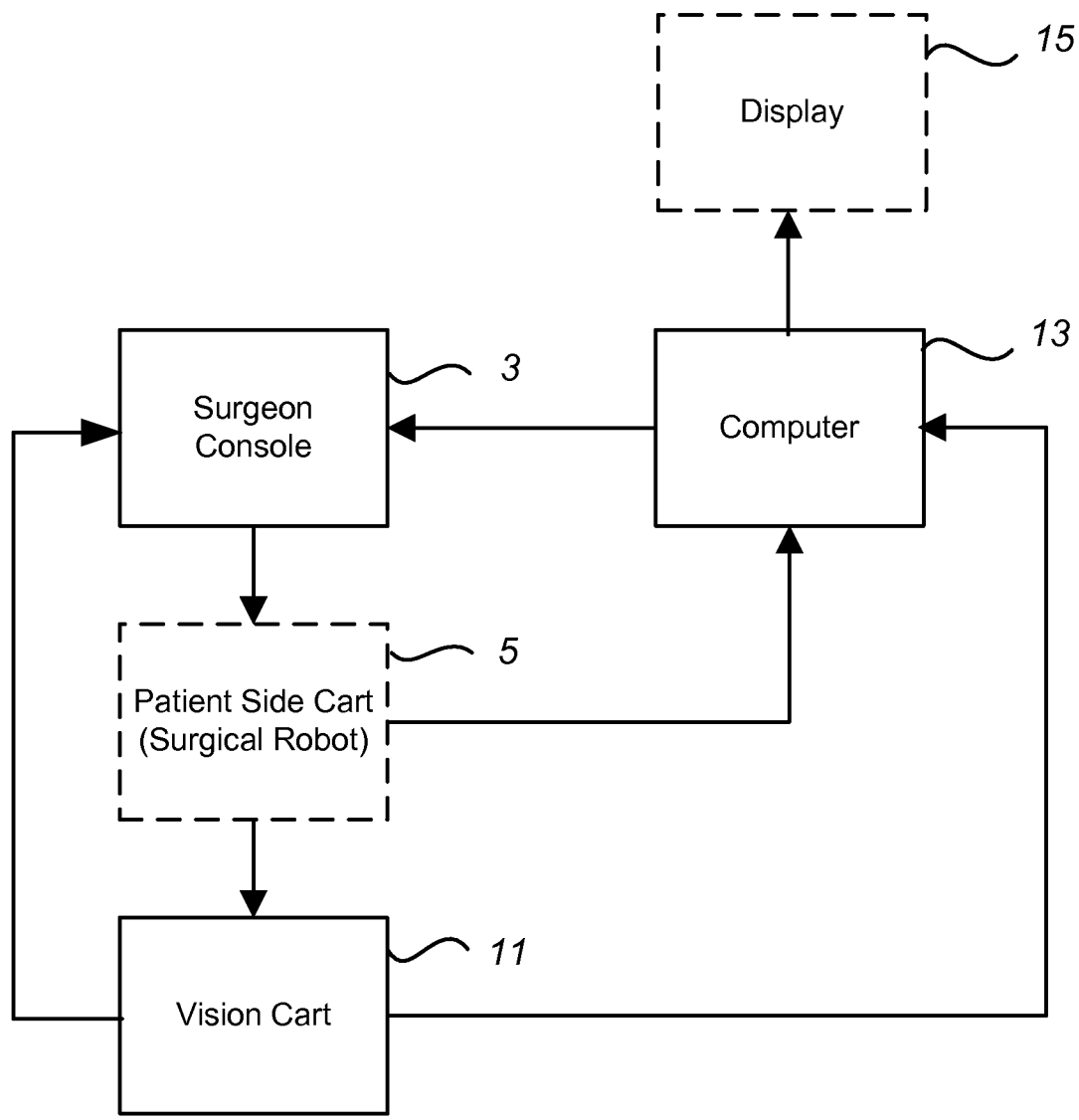
FIG. 3 is a block diagram representing components of the minimally invasive telesurgical system of FIG. 1.

FIG. 3 is a diagrammatic representation of the telesurgical system 1. As can be seen, the system includes the surgeon console 3, the patient side cart 5, and the vision cart 11. In addition, in accordance with an embodiment, an additional computer 13 and display 15 are provided. These components may be incorporated in one or more of the surgeon console 3, the patient side cart 5, and/or the vision cart 11. For example, the features of the computer 82 may be incorporated into the vision cart 11. In addition, the features of the display 15 may be incorporated into the surgeon console 3, for example, in the display 5, or maybe provided by a completely separate display or the surgeon console or on another location. In addition, in accordance with an embodiment, the computer 13 may generate information that may be utilized without a display, such as the display 15.

Figure 4:
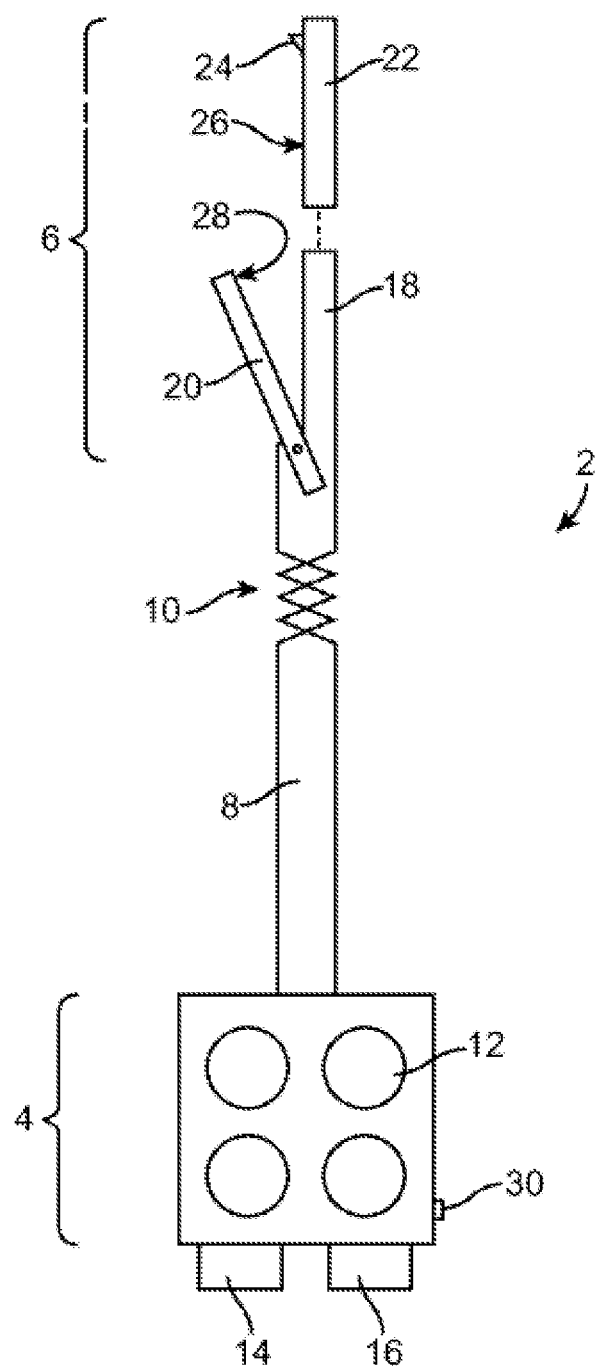
FIG. 4 is a diagrammatic view of a cut and seal surgical tool, in accordance with many embodiments.

FIG. 4 is a diagrammatic view of an exemplary cut and seal surgical instrument 2 in accordance with an aspect of the invention. As shown in FIG. 4, instrument 2 includes a force transmission mechanism 4 at the proximal end (outside the patient) and a combined cut and seal end effector 6 at the distal end (inside the patient; closer to the surgical site). Transmission mechanism 4 and cut and seal end effector 6 are coupled by instrument shaft 8. Cut and seal end effector 6 is optionally coupled to instrument shaft 8 via wrist mechanism 10. Instrument 2 is typically used to carry out minimally invasive surgery, during which end effector 6 and a distal part of shaft 8 are inserted into a patient via a small incision or natural orifice, typically through a cannula, to carry out a surgical procedure.

In the depicted embodiment, force transmission mechanism 4 includes disks 12, which mate to corresponding servomotors (not shown) when instrument 2 is mounted, e.g., for use in a surgical robotic system. The servomotors provide actuating forces to move components of instrument 2. Four disks 12 are shown; however, more or fewer may be used, depending on the desired actuated degrees of freedom for instrument 2. The servomotors are controlled by a surgeon moving a master manipulator, as described in more detail below. In addition, one or more servomotors 14, 16 may be mounted on instrument 2 itself to provide actuating forces for instrument 2 components. Shaft 8 is generally a hollow tube through which actuating cables run from transmission mechanism 4 to the components at the distal end of instrument 2. Such cables are illustrative of various ways (e.g., rods, rotating shafts, and the like) of moving instrument components. In some embodiments, shaft 8 rotates to provide roll to end effector 6. Shaft 8, and end effector 6, may have various outer diameters (e.g., 5 mm, 8 mm, 10 mm, 12 mm, etc.). Although shaft 8 is depicted as rigid, it is also illustrative of various flexible embodiments that may be used.

In the embodiment depicted in FIG. 4, cut and seal end effector 6 includes a stationary jaw member 18, a movable jaw member 20, and a removable cut and seal cartridge 22 that is removably coupled to stationary jaw member 18. Tissue is clamped between jaws 18 and 20 for cutting and sealing. Cut and seal cartridge 22 includes a movable knife 24 (e.g., a sharp blade or tissue cutter). Movable jaw member 20 may be actuated via a force transmitted through force transmission mechanism 4, or it may be actuated by one of the motors 14, 16 mounted on instrument 2. Similarly, knife 24 may be actuated via a force transmitted through force transmission mechanism 4 or by one of the motors 14, 16. In one aspect, a single motor 14 or 16 may be used to actuate both jaw 20 and knife 24. In one alternate aspect, jaw 18 may be movable and jaw 20 stationary, such that cartridge 22 is moved during instrument operation. In another alternate aspect, both jaws 18 and 20 are moveable.

End effector 6 also includes tissue sealing capability. A first tissue sealing electrode 26 is positioned on the inner face of cartridge 22. A second tissue sealing electrode 28 is positioned on jaw 20, opposing electrode 26. Electrodes 26, 28 are described in more detail below. Electrical energy for tissue sealing is provided to electrodes 26, 28 via an electrical coupling 30 at the proximal end of instrument 2. Electrical coupling 30 as depicted in FIG. 4 is illustrative of various positions at which it may be placed on the instrument, and it may require manual coupling to a tissue sealing energy source or it may couple automatically to the energy source when instrument 2 is mounted to a robotic manipulator for surgical operation. Alternatively, tissue sealing capability may be provided by other means, such as by stapling or suturing, which may be performed by the end effector.

Figure 5:
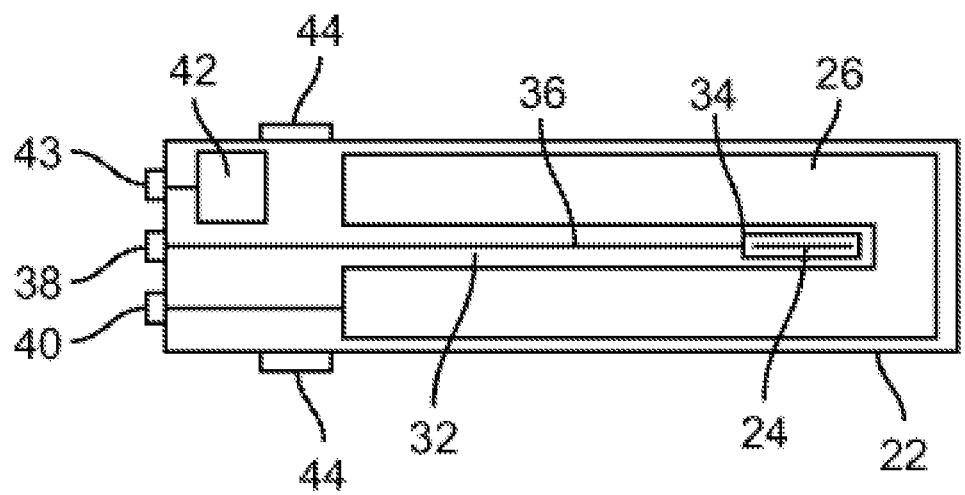
FIG. 5 is a diagrammatic top view of a removable cut and seal cartridge of a surgical tool, in accordance with many embodiments.

FIG. 5 is a diagrammatic top view of removable cut and seal cartridge 22. Electrode 26 is depicted in an elongated "U" shape so that it surrounds a slot 32 through which knife 24 moves. Various other electrode shapes or configurations may be used. In many aspects electrode 26 is positioned on both sides of slot 32 so that both free ends of a cut tissue (e.g., a blood vessel) are sealed before the tissue is cut between the two seals. FIG. 5 also shows that knife 24 is mounted on a sled 34 that moves as lead screw 36 rotates. Lead screw 36 is attached to a mechanical coupling 38 at the proximal end of cartridge 22, and coupling 38 attaches to a drive shaft when cartridge 22 is installed in instrument 2. Details of the coupling are described below. As described herein, knife 24 moves proximally to cut tissue. It is well understood, however, that knife 24 may move distally to perform its cutting action using a similar sled and lead screw operating mechanism.

FIG. 5 also shows that in some aspects cartridge 22 includes an electronic encryption device 42 (e.g., integrated circuit with data storage capability; in practice this is sometimes referred to as a "Dallas chip"). Electronic encryption device 42 may be used to convey information to the cut and seal control system (see below) about the cartridge type, if the cartridge has been used (to enforce one-time use restrictions), or the number of available lives for use (to manage multiple use restrictions (e.g., three uses)). Electronic encryption device 42 may also be used to ensure that a properly manufactured cartridge is being used. Electrical coupling 43 provides a connection point for encryption device 42. FIG. 5 also shows two snap fittings 44, which are illustrative of various ways of securely yet removably fastening removable cut and seal cartridge 22 in instrument 2.

Figure 6:
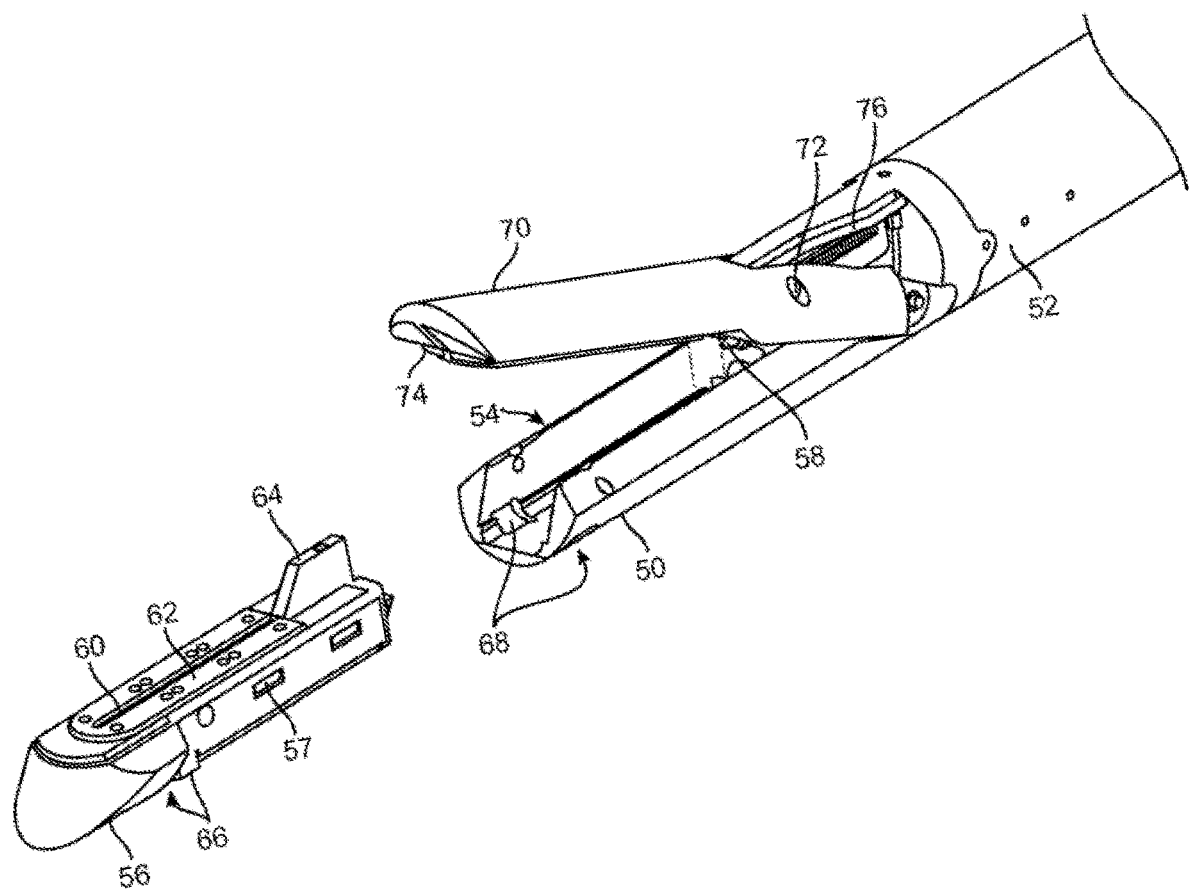
FIG. 6 is a perspective view of the distal end of a combined cut and seal minimally invasive surgical instrument, in accordance with many embodiments.

FIG. 6 is a perspective view of an embodiment of the distal end of a combined cut and seal minimally invasive surgical tool, generally described above as end effector 6, in accordance with many embodiments. FIG. 6 shows stationary jaw member 50 coupled to instrument shaft 52 (the optional wrist mechanism is omitted for clarity). A channel 54 in jaw member 50 receives removable cut and seal cartridge 56. Matching guide rails 57 and grooves (not shown) may be used in channel 54 and on cut and seal cartridge 56 to improve alignment and secure mounting. An illustrative electrical coupling 58 for cut and seal cartridge 56 is shown at the proximal end of channel 54 (in this perspective view, the mechanical and other electrical couplings are hidden). As cartridge 56 is secured in position within channel 54, the necessary electrical and mechanical couplings are automatically made.

As shown in FIG. 6, cut and seal cartridge 56 includes a tissue sealing electrode 60 that receives electrical tissue sealing energy via the electrical coupling in channel 54. A slot 62 in electrode 60 allows a knife (not shown) to rise above electrode 60's surface and move proximally (or distally) to cut tissue clamped between the jaw members. A raised tab 64 at the proximal end of cartridge 56 provides additional contact area for electrical connections, as well as a safety position for the tissue cutter, as described below. Fittings 66 (one is hidden) hold cartridge 56 in place in corresponding detents 68 in jaw member 50. Alternatively, cartridge 56 may also include a stapling mechanism for sealing the tissue prior to cutting. As can be appreciated from FIG. 6, the movement of the knife would not be visible to an endoscope or to a surgeon when moving within a clamped end effector. Movable jaw member 70 is coupled at hinge 72. Tissue sealing electrode 74 is shaped and positioned on jaw member 70 so that it is aligned with cut and seal cartridge electrode 60 when the cartridge is secured in channel 54. Electrode 74, and jaw member 70, includes a slot (not shown) to allow the tissue cutter in cartridge 56 to extend into jaw member 70 during cutting operations.

Figure 7:
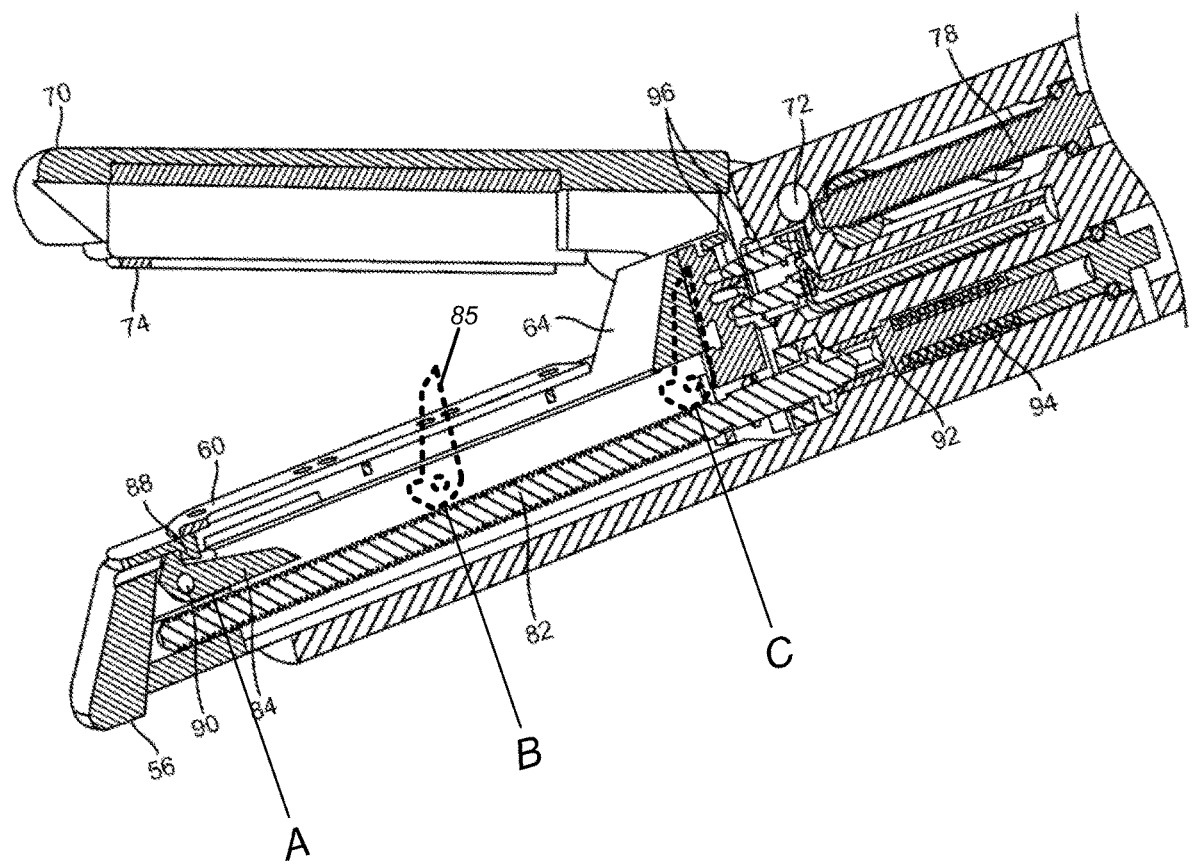
FIG. 7 is a side cross-sectional view of the embodiment of FIG. 6 showing different positions of the knife, in accordance with many embodiments.

FIG. 7 is a side cross-sectional view of the end effector embodiment depicted in FIG. 6, with the cut and seal cartridge securely positioned in the stationary jaw member. The embodiment shown in FIG. 7 is illustrative of working aspects of the distal end of the combined cut and seal end effector. As shown in FIG. 7, a first lead screw 78 operates movable jaw member 70. As lead screw 78 rotates (e.g., actuated by one of the motors 14, 16), a sliding member travels proximally moving jaw member 70 towards jaw member 50 to clamp tissue in between them. The use of the lead screw provides the strong clamping force sufficient for effective tissue sealing and cutting. When the tissue is clamped with sufficient force (clamping force feedback or other feedback may be used), the sealing and cutting operations may begin. During sealing, electrodes 60 and 74 receive electrical sealing energy to seal the clamped tissue. When sealing is complete, tissue cutting may begin.

A second lead screw 82 inside cut and seal cartridge 56 operates knife 84 having cutting edge 85 for cutting tissue. Knife 84 may comprise any member having a cutting edge sufficient to cut tissue. As lead screw 82 rotates, sled 86 moves knife 84 (i.e., a sharp blade) proximally from Position A to Position C to cut tissue clamped between the jaw members. As knife 84 starts to move, it engages tab 88, which causes knife 84 to rotate around hinge 90 and extend beyond the clamping surfaces of electrodes 60 and 74. Other ways of keeping the tissue cutting blade safe include, for example, surrounding it in a small raised covering when not in use. Tab 64 provides a safety position for knife 84 after it moves to its proximal position at Position C. In some aspects, after knife 84 has cut tissue, lead screw 82 may be rotated in the opposite direction to return knife 84 to its distal, ready to cut position. In this way, the cutting feature of removable cut and seal cartridge 56 may be reused, so that both the cutting and sealing operations may be performed more than once with a single cartridge. Such multiple use has a significant cost saving benefit.

Lead screw 82 is coupled to receive mechanical power (e.g., from one of motors 14, 16 (see FIG. 1)) via mechanical coupling 92. Mechanical coupling 92 includes a spring 94 that forces the coupling distally. When seal cartridge 56 is first fully inserted into jaw member 50, the mating mechanical couplings on the cartridge and in the jaw member may not be aligned (e.g., splines or various shapes may not be aligned). The force provided by spring 94 will move the instrument side coupling to fully engage the cartridge coupling as soon as it rotates into proper alignment.

FIG. 7 also illustrates three different positions of the knife, Position A, Position B, and Position C. In the current embodiment, knife 84 cuts as it moves proximally from Position A to Position C (as indicated by the arrows). As shown, the lead screw 82 actuates movement of the knife 84 along a longitudinal axis of the end effector. Although FIG. 7 depicts knife at the distal end of its path in Position A, during the cutting procedure knife 84 would move through various other positions, including Positions B and C (shown in dotted lines). In Position A, knife 84 is safely disposed within the distal portion of the cartridge. In position B, the knife has rotated around hinge 90 and travelled mid-way along its cutting path, its cutting edge 85 extending above the cartridge so as to cut tissue clamped within its path. In Position C, knife 84 is at the proximal end of its cutting path and is safely disposed in a proximal portion of the end effector, its cutting edge covered by tab 64. Tissue cutter 84 has a cutting edge 85 facing toward the proximal end of the end effector, such that knife 84 cuts clamped tissue when actuated to move from Position A to Position C. In an alternative embodiment, the cutting edge 85 may be disposed on knife 84 facing toward a distal portion of the end effector, such that the knife 84 would cut tissue when actuated to move distally from Position C to Position A. In some embodiments knife 84 may include a cutting edge facing in both directions, such that moving knife 84 in either direction would cut tissue clamped within the end effector.

In many embodiments, knife 84 includes a number of "positions" and may include positions other than those described in FIG. 7. For example, in an embodiment having a knife 84 that cuts tissue when moving distally, the knife may include a pre-cut position at Position C and a cut-complete position at Position A. Knife 84 may also include additional positions, such as any intermediate position between Positions A and C (e.g. Position B). Any such positions may be termed a "cut-incomplete position," since the knife 84 would have cut tissue along only part of the cutting path. The "knife positions" may also comprise an orientation of the knife. For example, Position B, as well as any position between A and C may be considered a "knife-exposed" position, indicating that the cutting edge 85 of knife 84 is exposed so as to cut tissue.

As can be see in FIG. 7, if for any reason, knife 84 were to stall during the cutting procedure, knife 84 would remain in a position between Position A and Position C, such as in Position B. If stalled in Position B, the cutting edge 85 of knife 84 would remain exposed, and subsequent movement of the knife 84 could potentially result in inadvertent cutting of tissue as the tool is withdrawn. Additionally, once the end effector was removed, if the surgeon was unaware that the cutting edge 85 was exposed, the cutting edge 85 could cut the hand of the surgeon, potentially exposing the surgeon to biological hazards. Such hazards might be avoided, however, through use of the claimed methods and systems.

In many embodiments, the tissue cutting and sealing systems described above are implemented in a minimally invasive surgical robotic system (e.g., a da Vinci® Surgical System). Typically, to carry out a procedure, the surgeon first moves an end effector of a surgical instrument into position at a surgical site and clamps tissue (e.g., a blood vessel) to be sealed and cut. Ideally, in order to achieve an effective tissue seal, the tissue should be clamped between the surgical instrument's electrodes with sufficient force (e.g., in the range of 100-150 psi). When the proper clamping force is achieved (automatically or under the surgeon's control), the surgeon commands the sealing operation which may include sending a signal to an electro-sealing unit or applying a force to fire a staple. When sealing is complete, the system may automatically generate a signal to the tool to begin the cutting operation without a separate cut command from the surgeon. Thus, combined cutting and sealing is carried out with a single command from the surgeon as the cut and seal controller controls both cutting and sealing aspects of the end effector. In additional aspects of the invention, a cut and seal controller may automatically send a signal to the end effector to either loosen or release the clamping force or may automatically send a signal to the end effector to reset the knife in preparation for another combined cut and seal actuation. The cut and seal controller may also command various combinations or all of these automatic actions in response to a single command signal from the surgeon. Further, the cut and seal controller may issue updated information to the electronic encryption device in instrument to effectively manage use restrictions, as described above.

Figure 8:
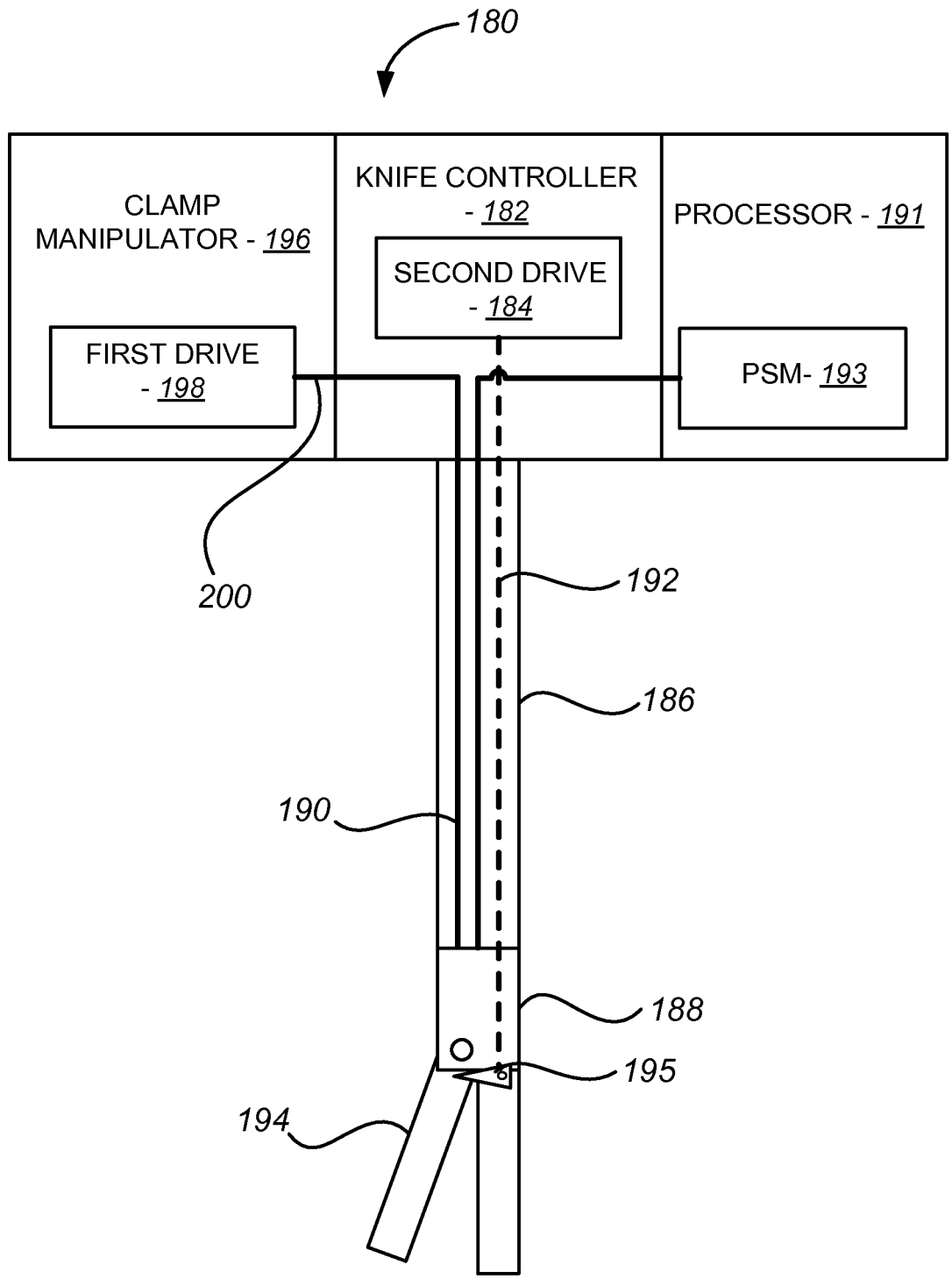
FIG. 8 is a diagrammatic view of a surgical tool, in accordance with many embodiments.

FIG. 8 schematically illustrates a robotic tool 180 in accordance with an embodiment of the present invention. The robotic tool 180 includes a clamp manipulator 196 with a first drive 198, a knife controller 182 with a second drive 184, a processor 191, a PSM 193, and an end effector 188. End effector 188 is coupled with the first and second drive through instrument shaft 186. Instrument shaft includes a first mechanism 190 operatively coupling first drive 198 with an opposable jaw 194 of end effector 188, such that when actuated opposable jaw 194 clamps a tissue. Instrument shaft further includes a second mechanism 192 operatively coupling second drive 184 with knife 195, such that, when actuated, knife 195 moves along a longitudinal axis of the jaws of the clamp cutting the clamped tissue. The clamp manipulator and knife are also coupled with a processor 191 and the surgeon's console. The processor 191 may determine a position of the end effector 188, jaw 194 of the end effector and knife 195 from positional information obtained by the PSM 193 (e.g. by tracking the kinematic chain). Once the positional data for each component is determined, processor 191 may send an output of the image of the tool and a visual indicator of a position of the knife to the display. As discussed above, the position of the knife may include an indication of a position and/or orientation of the knife 195 relative to end effector 188. The various positions may include but are not limited to a pre-cut position, a cut-complete position, a cut-incomplete position, and an exposed position, as discussed previously. Processor 191 may also determine the positions of the jaw 194 or the knife 195 from the displacement of the first or second mechanism 190, 192 or the motor displacement of the first drive 198 or second drive 184.

Figure 9:
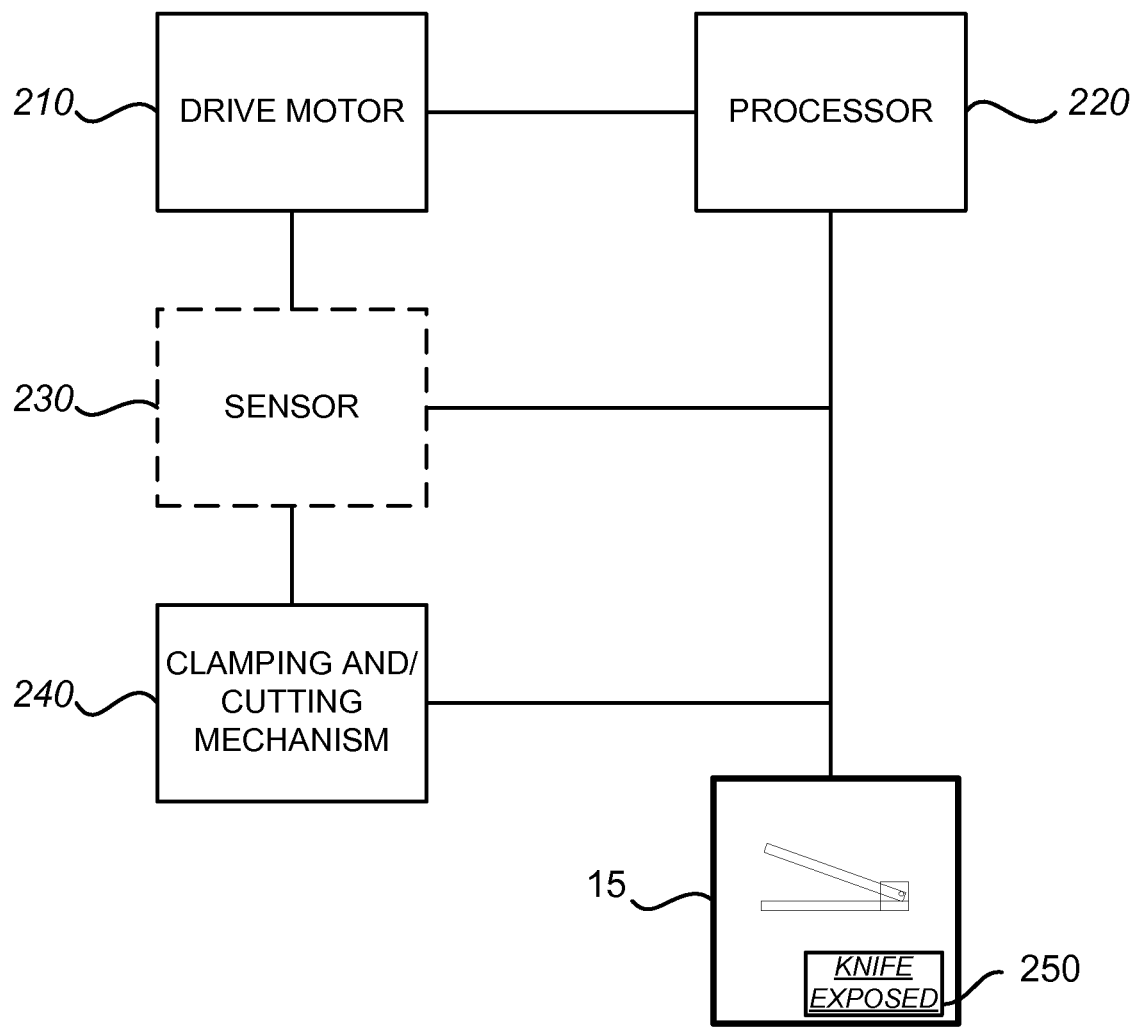
FIG. 9 is a diagrammatic view of a system, in accordance with many embodiments.

FIG. 9 is a diagrammatic view of a telerobotic surgical system in accordance with many embodiments. In the example of FIG. 9, a physician inputs a command to the system to clamp or cut a tissue. In response to the user command, the system begins driving motor 210 to drive clamping by actuating the jaws or to drive cutting of the tissue by moving the knife with mechanism 240. As mechanism 240 effects clamping or cutting, processor 220 receives positional information (or derivatives thereof) from sensor 230. The positional information may be derived from the displacement of the mechanism or motor, as described previously, or may obtained directly by the sensor 230, such as through detection of fiducial markers disposed on the jaws and/or knife. For example, positional markers may be placed on the jaws of the end effector and on the knife such that a sensor, such as an image capture device, can track movement of the knife relative to the end effector. The position of the element (e.g., knife) may also be tracked by a sensor 230 which is disposed on or near the element, such as by one or more electromagnetic position sensors or pressure sensitive sensors. Additionally, a green optical fiber may be incorporated into the knife mechanism to allow visualization of the knife location through detection of light emitted through the fiber. More information regarding the use of fiducial markers, as may be used in many embodiments of the present invention, can be found in commonly-owned U.S. application Ser. No. 12/428,657 entitled "Fiducial Marker Design and Detection for Locating Surgical Instrument in Images," filed on Apr. 23, 2009), the entirety of which is hereby incorporated by reference. Once the relative positions and/or configuration of the knife (also known as the knife position) have been determined, processor 220 outputs a visual indicator 250 of the knife position to be superimposed on the display 15 with an image of the end effector. Typically, display 15 includes images of the end effector and the visual indicator of knife position is superimposed on the display during cutting, and more preferably at all times during the procedure, such that the surgeon becomes accustomed to or habitualized with the position and movement of the knife during the cutting process.

Figure 10:
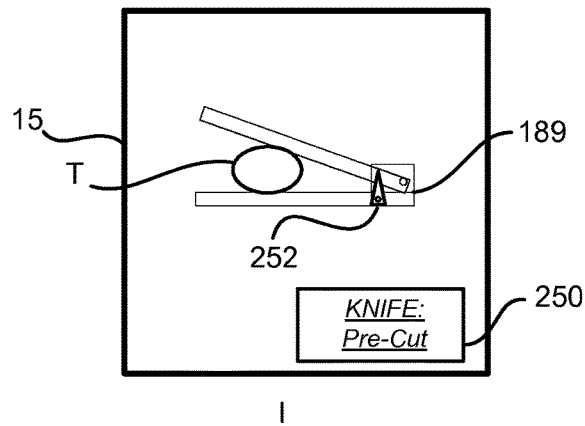
FIG. 10 illustrates a user interface display showing images of the tool with an indicator of knife position, in accordance with many embodiments.
Figure 10:
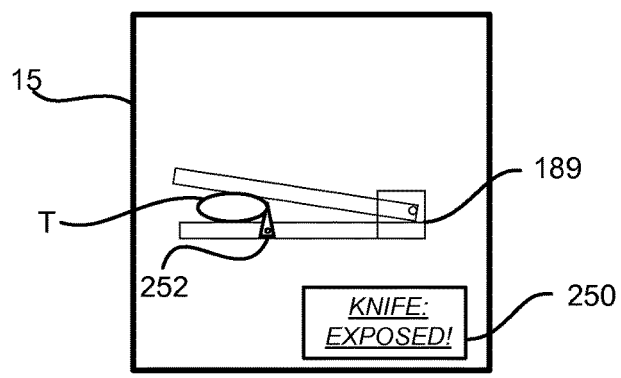
Figure 10:
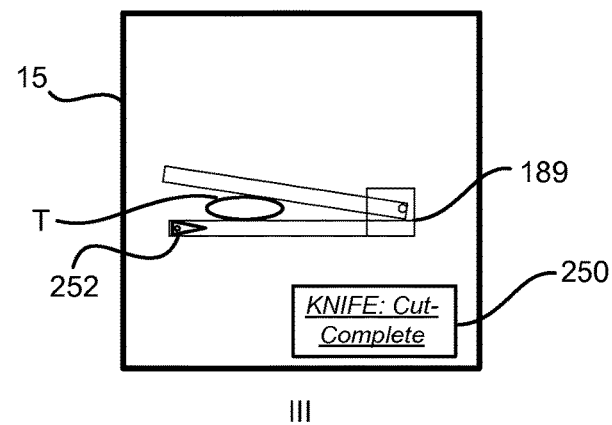

FIG. 10 illustrates three examples of visual indicator 250 showing a knife position on display 15, in accordance with an embodiment wherein the knife cuts tissue as it moves distally along the tool. The indicator of knife position is superimposed on the user interface display 15, which also display images and/or visual representations of the surgical tool end effectors during the cutting procedure. Indicator 250 may be any indicator (e.g. a light, text message, color change on display, etc.) sufficient to indicate a knife position to a user. Indicator 250 may include a synthetic representation 252 of the knife superimposed over either a synthetic representation or over an actual image of the tool shown on display 15. FIG. 10 shows three consecutive images of the end effector 189 on display 15 during a tissue cutting procedure in Frames I, II and III. In Frame I, the knife is in the pre-cut position disposed safely in the proximal portion of end effector 189, while indicator 250 shows the knife position as "Pre-Cut" and shows a synthetic representation 252 of the knife on the end effector. In Frame II, the knife has moved mid-way along the jaws of the end effector with the cutting edge of the knife exposed so as to cut tissue when moved distally. Indicator 250 shows a knife position indicator as "Knife: Exposed!" and the synthetic representation 252 midway along the tool. If for any reason, the knife should fail or stall as it moves from its pre-cut position to its cut-complete position, an optional warning may be output on the display. The warning may indicate the knife position as being "cut-incomplete," "exposed," or "stalled" (not shown). In Frame III, the knife has successfully moved the jaws of end effector 189 to its cut-complete position and has rotated so as to be safely disposed within the distal portion of end effector 189. Indicator 250 shows the knife position as "Cut-Complete" and the synthetic representation 252 depicting the location and orientation of the knife at its distal most position on end effector 189.

Knife Position Indicator with Tool Tracking

In some embodiments, the methods and systems may include tool tracking. In tool tracking a positional component is included in or is otherwise associated with the computer. The positional component provides information about a position of a tool, such as end effector 189, or an element, such as the knife. "Position" refers to at least one of the location and/or the orientation of the end effector. The position can be determined through the use of fiduciary markers, configuration markers or by tracking of the kinematic chain. A variety of different technologies, which may or may not be considered tool tracking devices, may be used to provide information about a position of an end effector. In a simple embodiment, the positional component utilizes a video feed from an image capturing device to provide information about the position of an end effector and/or the knife; however, other information may be used instead of, or in addition to, this visual information, including sensor information, kinematic information, or any combination thereof. Examples of systems that may be used for the tool tracking component are disclosed in U.S. Application Publication No. 2006/0258938, entitled, "Methods and System for Performing 3-D Tool Tracking by Fusion of Sensor and/or Camera Derived Data During Minimally Invasive Robotic Surgery"; U.S. Pat. No. 5,950,629, entitled "System for Assisting a Surgeon During Surgery"; U.S. Pat. No. 6,468,265, entitled "Performing Cardiac Surgery Without Cardioplegia"; and U.S. Application Publication No. 2008/0004603, entitled "Tool Position and Identification Indicator Displayed in a Boundary Area of a Computer Display Screen." The tool tracking component may utilize the systems and methods described in commonly owned U.S. application Ser. No. 12/428,657, entitled "Fiducial Marker Design And Detection For Locating Surgical Instrument In Images" and U.S. application Ser. No. 12/428,691, entitled "Configuration Marker Design and Detection for Instrument Tracking". In general, the positional component conveys information about the actual position and orientation of en end effector. This information is updated depending upon when the information is available, and may be, for example, asynchronous information.

Synthetic Knife Image at Actual Location of End Effector

In accordance with another embodiment, the synthetic knife image may be displayed over the actual location of a knife. This feature permits a surgeon S to follow the knife even when the knife is out of sight, for example when the knife is behind an organ or is covered by blood, such is often the case with the knife in a sealing and cutting instrument. Since the knife moves along the jaws of the end effector when the jaws are clamped on tissue, the knife is typically not visible with an endoscope as it is obscured by the jaws and/or the clamped tissue.

In accordance with an embodiment, the synthetic representation of the knife may be a two or three-dimensional model of the knife, and may be oriented so as to be consistent with the actual orientation of the knife relative to the tool. Thus, by using the claimed system and methods, the surgeon S would be aware of the position of the knife relative to the end effector throughout a procedure, which is particularly useful should the procedure stall or fail.

Figure 11:
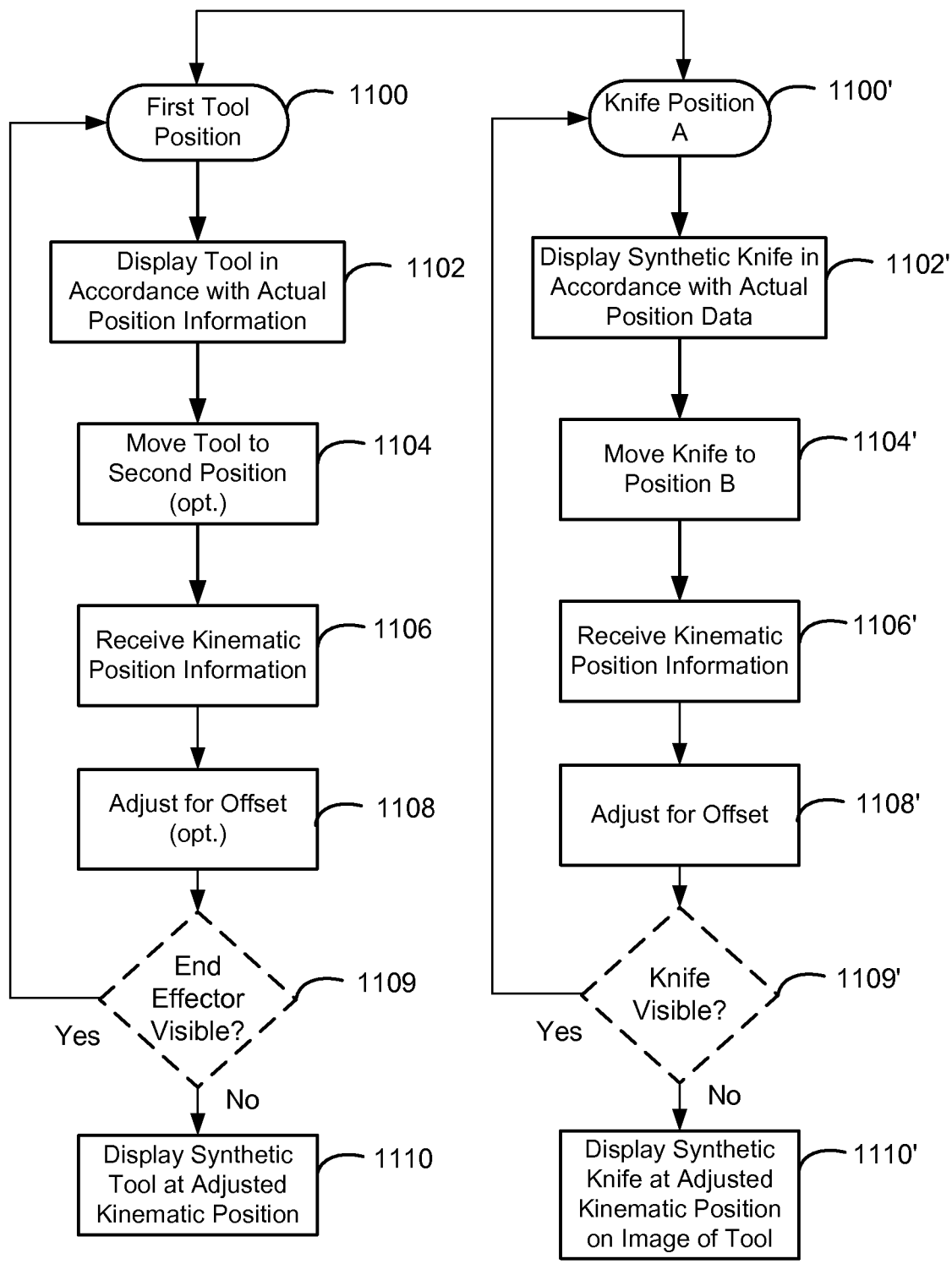
FIG. 11 is a diagrammatic view that illustrates a combined tissue cutting and sealing system using tool tracking, in accordance with many embodiments.

FIG. 11 is a flowchart showing steps for displaying a synthetic knife at the actual location of knife in accordance with many embodiments. Beginning at step 1100, the knife is in a first position. At step 1102, the synthetic representation of the knife is displayed over the image of the actual tool, which may be, for example, live video of the end effector tool. At step 1104, the knife moves to position B. Typically, the knife moves through position B on its way to a final position C (known as the cut-complete position). Kinematic position information is received at step 1106, and an adjustment for offset is taken in step 1108. At step 1109 if the end effector tool or knife is not visible from an endoscope, a synthetic image is displayed. Although typically, the end effector tool remains in the first position during the cutting process, if for any reason the tool moves, a similar tool tracking process optionally can be used to track the movement of the tool and display a synthetic representation of the end effector should the end effector tool no longer be visible. Since in its usual operation, the knife is obscured by the jaws of the end effector, the system will typically display the synthetic image of the knife tool. Thus, the synthetic image of the knife may be displayed on either an actual image of the end effector or on a synthetic image of the end effector, depending on whether the end effector is visible at any given time. At step 1110, the synthetic knife is displayed at the kinematically adjusted position of the tool. Thus, in accordance with the above described methods, the synthetic knife image is displayed on the image of the end effector, indicating the knife position of the knife during the cutting of tissue, and preferably at all times during cutting of the tissue.

Utilizing the method of FIG. 11, the movements of the synthetic knife matches the movements of the actual knife. Preferably, the movement of the synthetic knife is updated in real time so that the movement of the synthetic knife closely matches the movement of the actual tool so as to convey movement of the knife. As described above, although kinetic position information typically does not provide an accurate position of a knife in space, a change in position is relatively accurate. Thus, by utilizing the synthetic knife described with reference to FIG. 11, the position of the knife, can be followed fairly accurately, even when video or other position information for the tool is lost. As with previous embodiments, this synthetic representation of the knife for use in the method of FIG. 11 may be a three-dimensional model of the knife, or may be a line drawing of the knife or broken lines representing portions of the knife, or any other representation of the knife.

Figure 12:
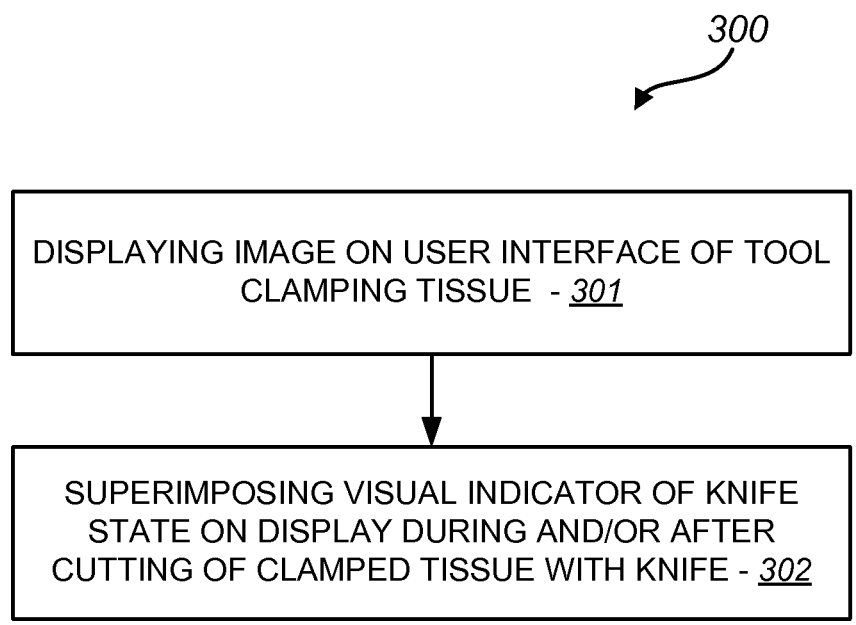
FIGS. 12-13 is a diagrammatic representation of methods, in accordance with many embodiments.
Figure 13:
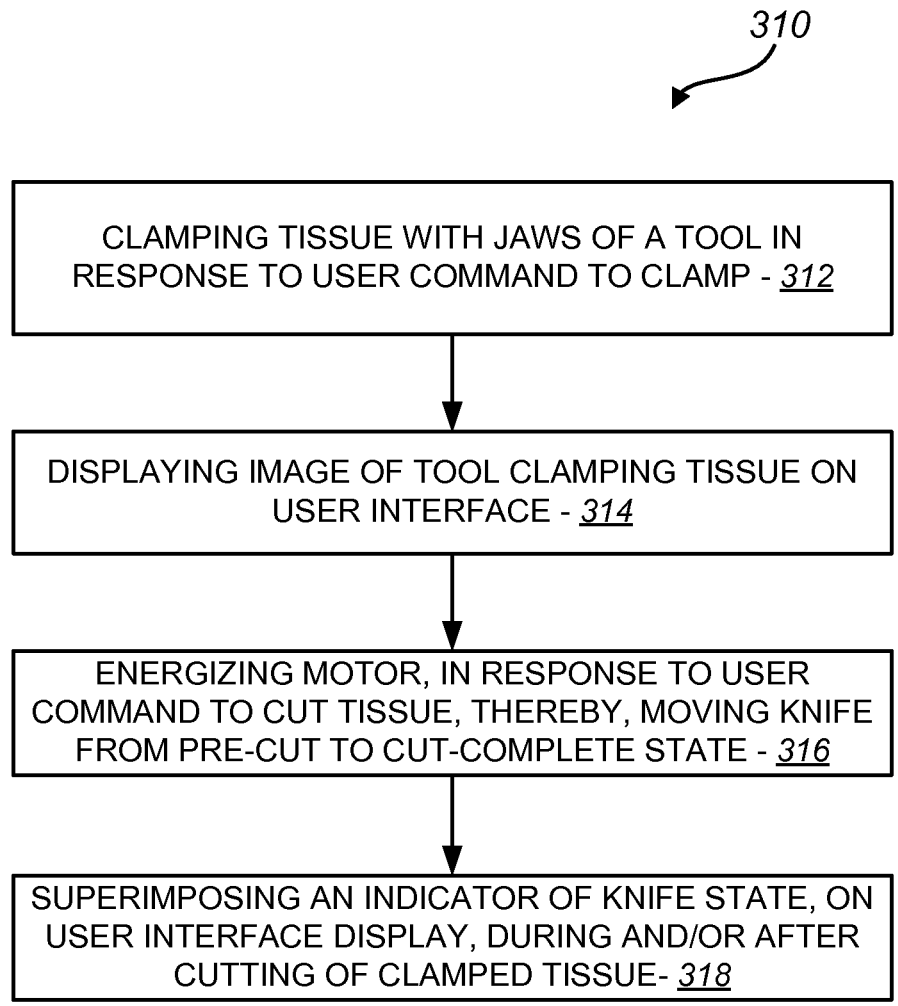

FIGS. 12-13 illustrate methods in accordance with many embodiments. Method 300, shown in FIG. 12, includes a step 301 of displaying an image on a user interface display of a tool clamping a body tissue and a step 302 of superimposing a visual indicator of knife position on the display during and/or after cutting of the clamped tissue with the knife. Method 310, shown in FIG. 13, includes a step 312 of clamping tissue with the jaws of a tool in response to a user command to clamp, a step 314 of displaying an image of the tool clamping the tissue on the user interface display, a step 316 of energizing the motor, in response to a user command to cut tissue, so as to move the knife from a pre-cut position to a cut-complete position to cut the tissue, and a step 318 of superimposing an indicator of knife position on the user interface display, during and/or after cutting of the clamped tissue.

Preferred embodiments of this invention have been described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications, alternative constructions and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A system comprising:
   an end effector having a jaw for clamping a material and a cutting element within the end effector; and
   a processor;
   wherein:
   the cutting element is moveable relative to the end effector;
   the cutting element is driven by a drive element and a mechanism coupling the drive element to the cutting element; and
   the processor is configured to:
   determine a position of the cutting element relative to the end effector based on a determined displacement of the drive element and a determined displacement of the mechanism; and
   display, on a user interface, an indicator of the position of the cutting element relative to the end effector.

2. The system of claim 1, wherein the processor is further configured to display a video image showing at least a portion of an environment of the end effector.

3. The system of claim 2, wherein the indicator is superimposed on the video image.

4. The system of claim 3, wherein the indicator comprises a synthetic representation of the cutting element.

5. The system of claim 1, wherein to display the indicator, the processor is configured to display the indicator in response to a trigger condition.

6. The system of claim 5, wherein the trigger condition comprises the cutting element stopping at an intermediate position during a movement between a pre-cut position and a cut-complete position.

7. The system of claim 1, wherein the indicator of the position of the cutting element shows at least one of a location of the cutting element or an orientation of the cutting element.

8. The system of claim 1, wherein the processor is further configured to display a second indicator of an orientation of the cutting element.

9. The system of claim 1, wherein the cutting element is rotated to extend beyond a grasping surface of the jaw when the cutting element is between a pre-cut position and a cut-complete position.

10. The system of claim 1, wherein the processor is further configured to update the display of the indicator in real time.

11. A method comprising:
    determining, by a processor, a position of a cutting element relative to an end effector based on a determined displacement of a drive element and a determined displacement of a mechanism, the end effector having a jaw for clamping a material, the cutting element being located within the end effector and being moveable relative to the end effector, the cutting element being driven by the drive element and the mechanism coupling the drive element to the cutting element; and
    displaying, on a user interface, an indicator of the position of the cutting element relative to the end effector.

12. The method of claim 11, further comprising displaying a video image showing at least a portion of an environment of the end effector.

13. The method of claim 12, further comprising superimposing the indicator on the video image.

14. The method of claim 13, wherein the indicator comprises a synthetic representation of the cutting element.

15. The method of claim 11, wherein displaying the indicator comprises displaying the indicator in response to a trigger condition.

16. The method of claim 15, wherein the trigger condition comprises the cutting element stopping at an intermediate position during a movement between a pre-cut position and a cut-complete position.

17. The method of claim 11, wherein the indicator of the position of the cutting element shows at least one of a location of the cutting element or an orientation of the cutting element.

18. The method of claim 11, further comprising displaying a second indicator of an orientation of the cutting element.

19. The method of claim 11, wherein the cutting element is rotated to extend beyond a grasping surface of the jaw when the cutting element is between a pre-cut position and a cut-complete position.

20. The method of claim 11, further comprising updating the displaying of the indicator in real time.

\* \* \* \* \*